United States Patent [19]

Wolter et al.

[11] Patent Number: 5,674,964
[45] Date of Patent: Oct. 7, 1997

[54] SELF-CURING SYSTEMS

[75] Inventors: Herbert Wolter, Gerchsheim-Grossrinderfeld; Helma Baeuerlein, Wuerzburg, both of Germany

[73] Assignee: Fraunhofer-Gesellschaft zur Foerderung der angewandten Forschung e.v., Munich, Germany

[21] Appl. No.: 442,589

[22] Filed: May 17, 1995

Related U.S. Application Data

[63] Continuation of Ser. No. 219,799, Mar. 29, 1994, abandoned.

[30] Foreign Application Priority Data

Apr. 1, 1993 [DE] Germany .................. 43 10 733.8

[51] Int. Cl.$^6$ .................................................. C08G 77/06
[52] U.S. Cl. .................. 528/18; 528/21; 528/24; 528/32; 526/279; 556/419; 556/420; 556/427; 556/404; 556/445
[58] Field of Search ........................ 556/419, 420, 556/427, 404, 445; 528/18, 32, 21, 24; 526/279

[56] References Cited

U.S. PATENT DOCUMENTS

| | | | |
|---|---|---|---|
| 5,399,738 | 3/1995 | Wolter et al. | 556/420 |
| 5,414,093 | 5/1995 | Wolter | 528/32 |

FOREIGN PATENT DOCUMENTS

| | | |
|---|---|---|
| 0 130 731 | 1/1985 | European Pat. Off. . |
| 0 298 734 | 1/1989 | European Pat. Off. . |
| 0 450 624 | 10/1991 | European Pat. Off. . |
| 0 450 625 | 10/1991 | European Pat. Off. . |
| 93 07230 | 4/1993 | WIPO . |

OTHER PUBLICATIONS

Derwent, Dialog File No. 351:Derwent WPI, Abstract of European Publication Patent No. 358011, (1990).
Derwent, Dialog File No. 351:Derwent WPI, Abstract of British Publication Patent No. 21378648, (1984).
Derwent, Dialog File No. 351:Derwent WPI, Abstract of German Publication Patent No. 3100555, (1981).
Derwent, Dialog File No. 351:Derwent WPI, Abstract of European Publication Patent No., 230342, (1987).
Derwent, Dialog File No. 351:Derwent WPI, Abstract of European Publication Patent No., 171493, (1985).

Primary Examiner—Melvyn I. Marquis
Attorney, Agent, or Firm—Foley & Lardner

[57] ABSTRACT

The invention relates to self-curing systems based on polymerizable and hydrolytically condensable or condensed silicon compounds. The systems according to the invention comprise one or more components which contain starter and/or activator systems, at least one component of the system containing a silicon compound of the formula I or Ia, or a precondensed form thereof, $$\{X_aR_bSi[R'(A)_c]_{(4-a-b)}\}_xB \quad (I)$$

$$\{X_aR_bSi[(R'A)_c]_{(4-a-b)}\}_xB \quad (Ia)$$

The invention furthermore relates to activators in the form of silane-bonded tertiary amines of the general formula IX or X.

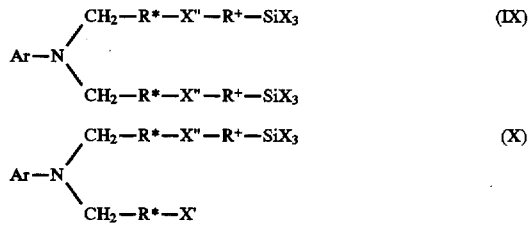

20 Claims, No Drawings

SELF-CURING SYSTEMS

This application is a continuation of application Ser. No. 08/219,799, filed Mar. 29, 1994 now abandoned.

FIELD OF THE INVENTION

The invention relates to self-curing systems placed on polymerizable and hydrolytically condensable or condensed silicon compounds. The systems according to the invention comprise one or more components which contain starter (initiator) and/or activator systems, and if appropriate customary additives and/or fillers and if appropriate further copolymerizable monomers and/or oligomers and/or hydrolytically co-condensable compounds. The invention furthermore relates to the separation of these systems and their use. The present invention particularly relates to self-curing systems based on acrylates and/or methacrylates, their preparation and their use.

The invention furthermore relates to novel, silane-bonded, tertiary amines of the general formula IX or X, which can be employed as activators for self-curing.

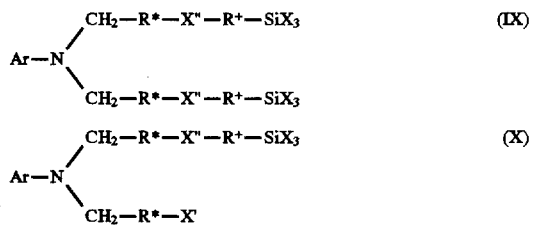

BACKGROUND OF THE INVENTION

A large number of self-curing plastics have been known for a long time. Such systems are used for the most diverse purposes, for example as molding compositions, as materials for coatings, etc. Because of these diverse possible uses, however, there is also a constant demand for modification of the already known systems, on the one hand thereby to open up new fields of use, and on the other hand to optimize the properties thereof still further for certain intended uses.

Self-curing systems comprise one or more components and contain, inter alia, reactive monomers which polymerize by means of various starter/activator systems and thus harden. In the case of two-component materials, for example, one component contains an activator and the second component contains a starter, and when the two components are brought together and mixed, the reactive monomers polymerize and the system cures. Acrylates and methacrylates of various structures, for example, are employed as reactive monomers, aromatic amines, such as N,N-dimethyl-p-toluidine, for example, are employed as activators and dibenzoylperoxide (DBP), for example, is employed as the starter. Other initiator/activator systems are also know.

Pigments, stabilizers, plasticizers or impact improvers as well as fillers of the most diverse nature are added as customary additives to the self-curing systems.

A decisive disadvantage of the self-curing systems based on acrylates or methacrylates is to be found in the methacrylate and acrylate monomers. Above all, low molecular weight acrylate and methacrylate monomers often cause an acute toxic action, in addition to a severe odor nuisance.

Another great disadvantage of the self-curing systems according to the prior art is that if amines are used as activators, these are still present and mobile in the system after curing, which leads to major toxicological problems and in particular virtually excludes use of the self-curing systems in the medical sector.

Because of the many possible uses of self-curing systems, together with the most diverse requirements of these, there is still room for new developments.

SUMMARY OF THE INVENTION

The object of the present invention is therefore to provide further self-curing systems. These systems should be universally applicable and easy to handle, and they should be curable with known starter/activator systems and flexible in processing and application time, e.g., they should have adjustable curing times of between one and about 30 minutes. Thus, for example, self-curing systems for gluing should cure rapidly and those for the production of shaped articles should cure slowly. Furthermore, it should be possible to provide these systems with additives and fillers, and they should be miscible with thermally and/or UV-curable systems or components in wide ranges. In addition, it should be possible to incorporate these systems into an organic-inorganic network, and the constituents of the system, in particular the reactive monomers, should be toxicologically acceptable.

Another object of the present invention is to provide such self-curing systems which can be cured with toxicologically acceptable activators, so that use of these systems in the medical sector becomes possible.

At least one of the foregoing objects in achieved by means of a self-curing composition comprising polymerizable and hydrolytically condensable and/or condensed compounds of silicon. In one embodiment, a self-curing composition comprises (i) a starter or activator, and (ii) at least one silicon compound of the formula I or Ia, or a precondensed form thereof,

in which the radicals and indices are identical or different and have the following meaning:

A=O, S, PR", POR", NHC(O)O or NHC(O)NR",
B=a straight-chain or branched organic radical which is derived from a compound B', said compound B' comprising at least 5 to 50 carbon atoms, and having at least two C=C double bonds, except when c=1 and A=NHC(O)O or NHC(O)NR" in which case compound B' comprises at least one double bond,
R=alkyl, alkenyl, aryl, alkylaryl or arylalkyl,
R'=alkylene, arylene or alkylenearylene,
R"=hydrogen, alkyl or aryl,
X=hydrogen, halogen, hydroxyl, alkoxy, acyloxy, alkylcarbonyl, alkoxycarbonyl or NR"$_2$,
a=1, 2 or 3,
b=0, 1 or 2,
c=0 or 1,
x=an integer, the maximum value of which corresponds to the number of double bonds in the compound B' minus 1, or equals the number of double bonds in the compound B', if c=1 and Z represents NHC(O)O or NHC(O)NR";

wherein the above alkyl and alkenyl radicals are optionally substituted straight-chain, branched or cyclic radicals having from 1 to 20 carbon atoms, aryl represents optionally substituted phenyl, naphthyl or biphenyl, and the above alkoxy, acyloxy, alkylcarbonyl, alkoxycarbonyl, alkylaryl, arylalkyl, arylene, alkylene and alkylenearyl radicals are derived from the alkyl and aryl radicals defined above.

If appropriate, the composition may comprise customary additives and/or fillers and, if appropriate, further copolymerizable monomers and/or oligomers and/or further hydrolytically condensable and/or condensed compounds of silicon and, if appropriate, other elements from the group consisting Al, Ti, Zr, B, P, Sn, Pb, the transition metals, the lanthanides and the actinides.

Another embodiment provides activators in the form of silane-bonded tertiary amines of the general formula IX or X,

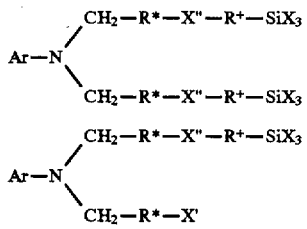

in which the radicals have the following meaning:
Ar=aryl;
R*=alkylene having 1 to 10 C atoms,
R+=alkylene having 0 to 10 C atoms,
X=hydrogen, halogen, hydroxyl, alkoxy, acyloxy, alkylcarbonyl, alkoxycarbonyl or $NR''_2$,
X'=—OH, —$NH_2$, —SH, —CH=$CH_2$, —C(O)—O—C(O)—$R^-$,

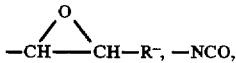

$R^-$=alkyl with 1 to 10 C atoms,
X"=—O—C(O)—NH—, —NH—C(O)—NH—, —S—C(O)—NH—, —O—$CH_2$—CHOH—, —NH—$CH_2$—CHOH—, —S—$CH_2$—CHOH—, —O—C(O)—, —NH—C(O)—, —S—C(O)—, —$C_2H_4$—, —$C_2H_4$—S—, —$C_2H_4$—NH—, —NH—C(O)—O—, —NH—C(O)—S—, —CHOH—$CH_2$—O—, —CHOH—$CH_2$—NH—, —CHOH—$CH_2$—S—, —C(O)—O—, —C(O)—NH—, —C(O)—S—,
wherein one or more of Ar, R*, $R^-$ or R+ may be substituted.

Also provided is a method of making a self-curing composition comprising combining an activator as described above with polymerizable monomers, oligomers, polymers, or mixtures thereof. Another embodiment provides a method of using such an activator in a self-curing composition.

Another embodiment provides a method of using a self-curing composition according to this invention in a process such as casting, adhering, sealing coating, shaping, preparation of fillers, molding, bonding, and producing fibers or films.

Yet another embodiment provides a method of making a self-curing composition comprising combining (i) a starter or activator, and (ii) a silicon compound of the formula I and/or Ia, described above.

DESCRIPTION OF PREFERRED EMBODIMENTS

Surprisingly, it has been found that the silanes of the formula I and Ia are exceptionally suitable for use as reactive monomers in self-curing systems. The C=C double bonds of the silane-bonded radicals B allow rapid curing via organic polymerization, after addition of suitable activator/starter systems, it being possible to control the rate of reaction, i.e., the curing time, via the starter/activator concentration and via the ratio thereof.

The curing time furthermore can be controlled via the number and reactivity of crosslinkable components or crosslinkable groups, for example the acrylate groups. It is thus possible to employ the systems according to the invention both for the production of shaped particles, where long curing times are desired, and for adhesive bonds, where rapid curing is required. The systems according to the invention hold an extensive potential for variation with respect to their use.

Another advantage of the systems according to the invention is that the silylalkoxy groups of the silanes of the formula I and Ia offer the possibility of building up an inorganic network in accordance with the principles of the sol-gel process, it being possible for further inorganically crosslinking components to be incorporated into this network, which can thus be varied within wide ranges and can be adapted easily and universally to the requirements of the particular case of use.

An advantage of the systems according to the invention further more is that an organic-inorganic network is built up via the silylalkoxy groups and via the C=C double bonds of the silanes of the formula I and Ia, and this can likewise be varied within wide ranges and likewise can be adapted easily and universally to the requirements of the particular case of use. Thus, for example, further copolymerizable, self-curing and thermally and/or UV-curable monomers can be added to the systems according to the invention in order thus to adapt their chemical and physical properties to the requirements of the particular case of use.

The self-curing systems according to the invention provide materials which allow preparation of inorganic-organic composite polymers with the most diverse properties. These various properties can be adjusted, for example, via the structural relationships within the silanes of the formula I and Ia employed, and by the structural relationships of the copolymerizable monomers and of the further cohydrolyzable components.

The self-curing systems according to the invention can be employed either as such or in the form of solutions in boding (for example of optical-electronic components) as adhesives or adhesion promoters for the most diverse substrates, and furthermore for surface sealing of conventional composites, as adhesives, composites or bulk materials, as casting, sealing and coating compositions or in the shaping processes or molding (for example in replication). The systems according to the invention moreover can be employed for the production of fibers, films or fillers. Furthermore, if reactive acrylate or methacrylate groups are employed, rapid and complete curing is allowed, it being possible for the curing times to be controlled by the number and reactivity of these groups. Moreover, a combination of self-curing with, for example, photo-induced or thermal curing is possible.

Another advantage of the self-curing systems according to the invention over the prior art is that polymerizable, toxic monomers, for example toxic acrylates or methacrylates, are firmly bonded to the silanes of the formula I and/or Ia and are thereby firmly embedded in the inorganic-organic network so that, even in the event of incomplete polymerization, no free monomers can be present after curing. In the case of the self-curing systems according to the prior art based on acrylates and methacrylates, however, there is still the danger that free monomers which can lead to considerable toxic problems are still present after curing because of incomplete polymerization.

There is therefore the possibility of also employing the systems according to the invention in the medical sector. One possible use is, for example, use as intraocular lens filling material in combating cataracts and other eye diseases. Reference is made to DE 3927667 A1 with regard to further details in this context.

The silanes of the formula I and Ia can be polymerized by the radicals B and hydrolyzed by the radicals X. An inorganic network with Si—O—Si units can be built up via the hydrolyzable groups, while the double bonds contained in the radical B polymerized to build up an organic network.

The alkyl radicals are, for example, straight-chain, branched or cyclic radicals having 1 to 20, in particular 1 to 10, carbon atoms and preferably lower alkyl radicals having 1 to 6, particularly preferably 1 to 4, carbon atoms. Specific examples are methyl, ethyl, n-propyl, i-propyl, n-butyl, i-butyl, s-butyl, t-butyl, n-pentyl, n-hexyl, cyclohexyl, 2-ethylhexyl, dodecyl and octadecyl.

The alkenyl radicals are, for example, straight-chain, branched or cyclic radicals having 2 to 20, preferably 2 to 10, carbon atoms and preferably lower alkenyl radicals having 2 to 6 carbon atoms, such as, for example, vinyl, allyl and 2-butenyl.

Preferably aryl radicals are phenyl, biphenyl and naphthyl. The alkoxy, acyloxy, alkylamino, dialkylamino, alkylcarbonyl, alkoxycarbonyl, arylalkyl [sic], alkylaryl, alkylene and alkylenearylene radicals are preferably derived from the abovementioned alkyl and aryl radicals. Specific examples are methoxy, ethoxy, n- and i-propoxy, n-, i-, s- and t-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The radicals mentioned can optionally carry one or more substituents, for example halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxyl, formyl, carboxyl, mercapto, cyano, isocyanato, nitro, epoxy, $SO_3H$ or $PO_4H_2$.

Among the halogens, fluorine, chlorine and bromine, in particular chlorine, are preferred.

For a $\geq 2$ or b=2, the radicals X and R can in each case have the same or a different meaning.

In preferred embodiments of the self-curing systems according to the invention, the radicals X, R, R', A, a, b, c and x in the general formula I and Ia are defined as follows:
X: $(C_1-C_4)$-alkoxy, in particular methoxy and ethoxy; or halogen, in particular chlorine;
R: $(C_1-C_4)$-alkyl, in particular methyl and ethyl;
R': $(C_1-C_4)$-alkylene, in particular methylene and propylene;
A: O, S or NHC(O)O, in particular S or NHC(O)O;
a: 1, 2 or 3;
c: 0 or 1, preferably 1,
4−a−b: 0 for c=0 and 1 for c=1;
x: 1 or 2.

In particularly preferred embodiments of the systems according to the invention, the structural unit with the index x in the general formulae I and Ia is chosen from triethoxysilyl, methyldiethoxysilyl, methyldichlorosilyl, 3-methyldimethoxysilyl-propylthio, 3-triethoxysilyl-propylthio, ethoxydimethylsilyl-methylthio, methyldiethoxysilyl-methylthio [sic] or 3-triethoxysilylpropylurethane.

The radical B in the general formulae I and Ia is derived from a substituted or unsubstituted compound B', having at least one or at least two C=C double bonds, for example containing vinyl, allyl, acryl and/or methacryl groups, and having 5 to 50, preferably 6 to 30, carbon atoms. B is preferably derived from a substituted or unsubstituted compound B' having two or more acrylate and/or methacrylate groups. Such compounds are called (meth)acrylates below.

If the compound B' is substituted, the substituents can be chosen from among the abovementioned substituents.

In further preferred embodiments of the systems according to the invention, silanes of the general formula I and/or Ia are employed in which B is derived from acrylic acid esters of trimethylolpropane, pentaerythritol, dipentaerythritol, $C_2-C_4$-alkanediols, for example of glycerol (for example glycerol dimethacrylate), polyethylene glycols or polypropylene glycols, or of optionally substituted and/or alkoxylated bisphenol A.

Concrete examples of silanes of the general formulae I and Ia, and their preparation can be found in German Patent 40 11 044 C2 and published EP 0451709 A2, respectively, the disclosure of which are expressly incorporated herein by reference.

In addition to the silanes of the general formulae I and Ia, further hydrolytically condensable compounds of silicon or other elements from the group comprising Al, Ti, Zr, B, P, Sn, Pb, the transition metals, the lanthanides and the actinides, either as such or already in precondensed form, can also be used for the preparation of the systems according to the invention.

It is preferable for at least 50 mol %, in particular at least 80 mol %, and specifically at least 90 mol %, based on the monomeric compounds, of the starting materials used for preparation of the systems according to the invention to be silicon compounds. It is likewise preferable for the systems according to the invention to be based on at least 10 mol %, for example 25 to 100 mol %, in particular 50 to 100 mol % and specifically 75 to 100 mol %, in each case based on the monomeric compounds, of one or more of the silanes of the general formula I and/or Ia.

Preferred hydrolytically condensable silicon compounds which differ from silanes of the general formulae I and Ia and can optionally be employed are those of the general formula II,

$$R_a(R^2Z)_b SiX_{4-(a+b)} \quad (II)$$

in which the radicals R, $R^2$ and Z are identical or different and have the following meaning:
R=alkyl, alkenyl, aryl, alkylaryl or arylalkyl,
$R^2$=alkylene or alkenylene, it being possible for these radicals to be interrupted by oxygen atoms or sulfur atoms or —NH— groups,
X=hydrogen, halogen, hydroxy, alkoxy, acyloxy, alkylcarbonyl, alkoxycarbonyl or $NR''_2$, where R''=hydrogen, alkyl or aryl,
Z=halogen or an optionally substituted amino, amide, aldehyde, alkylcarbonyl, carboxyl, mercapto, cyano, alkoxy, alkoxycarbonyl, sulfonic acid, phosphoric acid, acryloxy, methacryloxy, epoxy or vinyl group,
X=0, 1, 2 or 3,
Y=0, 1, 2, or 3, where x+y=1, 2 or 3.

Silanes of the general formula II are either commercially obtainable or can be prepared by known methods; cf., W.

Noll, "Chemie und Technologie der Silicone" ("Chemistry and Technology of the Silicones"), Verlag Chemie GmbH, Weinheim/Bergstraβe (1968). Reference is furthermore made to German Patent 40 11 044 C2 and to DE 34 07 087 C2.

The alkyl radicals are, for example, straight-chain, branched or cyclic radicals having 1 to 20, preferably 1 to 10, carbon atoms, and particularly preferably are lower alkyl radicals having 1 to 6 carbon atoms. Specific examples are methyl, ethyl, n-propyl, i-propyl, n-butyl, s-butyl, t-butyl [sic], i-butyl, n-pentyl, n-hexyl, cyclohexyl, 2-ethylhexyl, dodecyl and octadecyl.

The alkenyl radicals are, for example, straight-chain, branched or cyclic radicals having 2 to 20, preferably 2 to 10, carbon atoms, and particularly preferably are lower alkenyl radicals having 2 to 6 carbon atoms, such as, for example, vinyl, allyl or 2-butenyl.

Preferred aryl radicals are phenyl, biphenyl and naphthyl.

The alkoxy, acyloxy, alkylcarbonyl, alkoxycarbonyl and amino radicals are preferably derived from the abovementioned alkyl and aryl radicals. Specific examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The radicals mentioned can optionally carry one or more substituents, for example halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, isocyanato, nitro, epoxy, $SO_3H$ and $PO_4H_2$.

Among the halogens, fluorine, chlorine and bromine are preferred.

Specific examples of hydrolytically condensable silanes of the general formula II are:

$CH_3-Si-Cl_3$, $CH_3-Si-(OC_2H_5)_3$, $C_2H_5-Si-Cl_3$,
$C_2H_5-Si-(OC_2H_5)_3$, $CH_2=CH-Si-(OC_2H_5)_3$,
$CH_2=CH-Si-(OC_2H_4OCH_3)_3$, $(CH_3)_2-Si-Cl_2$,
$CH_2=CH-Si-(OOCCH_3)_3$, $(CH_3)_2-Si-(OC_2H_5)_2$,
$(C_2H_5)_3-Si-Cl$, $(C_2H_5)_2-Si-(OC_2H_5)_2$,
$(CH_3)_2(CH_2=CH)-Si-Cl_2$, $(CH_3)_3-Si-Cl$,
$(t-C_4H_9)(CH_3)_2-Si-Cl$,
$(CH_3O)_3-Si-C_3H_6-NH-C_2H_4-NH-C_2H_4-NH_2$,
$(CH_3O)_3-Si-C_3H_6-SH$,
$(CH_3O)_3-Si-C_3H_6-NH-C_2H_4-NH_2$,
$(CH_3O)_3-Si-C_3H_6-Cl$,
$(CH_3O)_3-Si-C_3H_6-O-C(O)-C(CH_3)=CH_2$,
$(CH_3)_2(CH_2=CH-CH_2)-Si-Cl$,
$(C_2H_5O)_3-Si-C_3H_6-NH_2$, $(C_2H_5O)_3-Si-C_3H_6-CN$,

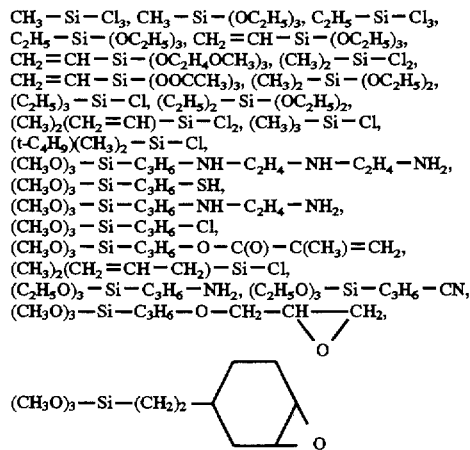

Furthermore, preferred hydrolytically condensable silicon compounds which differ from silanes of the general formulae I and Ia and can optionally be employed are likewise those of the general formula III, $$Y_nSiX_mR_{4-(n+m)} \quad (III)$$

in which the radicals X, Y and R are identical or different and have the following meaning:

R=alkyl, alkenyl, aryl, alkylaryl or arylalkyl,

X=hydrogen, halogen, hydroxy, alkoxy, acyloxy, alkylcarbonyl, alkoxycarbonyl or $NR''_2$, where R''=hydrogen, alkyl or aryl, Y=a substituent which contains a substituted or unsubstituted 1,4,6-trioxaspiro-[4,4]nonane radical, n=1, 2 or 3, m=1, 2 or 3, where n+m≦4.

The silanes of the general formula III, like the silanes of the general formulae I and Ia, are hydrolyzable and polymerizable and, like the silanes of the formulae I and Ia, can be incorporated into an organic-inorganic network. Silanes of the general formula III furthermore are stable compounds which can be hydrolyzed and condensed in a basic medium without the spiro complex being prematurely opened. They furthermore offer the great advantage that the shrinkage properties of the systems according to the invention during curing, i.e. during polymerization, is influenced by their addition such that no or only slight shrinkage occurs and expansion is even possible.

The radicals X and R of the general formula III are as defined in the general formula II. Concrete examples of silanes of the general formula III and their preparation can be found in DE 4125201 C1.

Particularly preferred hydrolyzable aluminum compounds which are optionally used for preparation of the systems according to the invention are those which have the general formula IV, $$AlR°_3 \quad (IV)$$

in which the radicals R°, which can be identical or different, are chosen from halogen, alkoxy, alkoxycarbonyl and hydroxyl. Reference may be made to the statements in connection with the suitable hydrolyzable silicon compounds with respect to the more detailed (preferred) definitions of these radicals. The groups just mentioned can also be replaced in total or in part by chelating ligands (for example acetylacetone or acetoacetic acid ester, acetic acid).

Particularly preferred aluminum compounds are the aluminum alkoxides and halides. Concrete examples which may be mentioned in this connection are $Al(OCH_3)_3$, $Al(OC_2H_5)_3$, $Al(O-n-C_3H_7)_3$, $Al(O-i-C_3H_7)_3$, $Al(OC_4H_9)_3$, $Al(O-i-C_4H_9(_3$, $Al(O-s-C_4H_9)_3$, $AlCl_3$ and $AlCl(OH)_2$. Compounds which are liquid at room temperature, such as, for example, aluminum sec-butylate and aluminum isopropylate, are particularly preferred.

Suitable hydrolyzable titanium and zirconium compounds that can be employed according to the invention are those of the general formula V, $$MX_kR_l \quad (V)$$

in which is M titanium or zirconium and the radicals R and X are identical or different and are as defined in the case of the general formulae I and Ia. This also applies to the preferred meanings. k represents an integer from 1 to 4, in particular 2 to 4, and l represents 0, 1, 2 or 3, preferably 0, 1 or 2. The compounds of the formula V are particularly preferably those in which k is 4.

Al in the case of the above Al compounds, complex Ti or Zr compounds can also be employed. Additional preferred complexing agents here are acrylic acid and methacrylic acid.

Concrete examples of Zr and Ti compounds which can be employed are $TiCl_4$, $Ti(OC_2H_5)_4$, $Ti(OC_3H_7)_4$, $Ti(O-i-C_3H_7)_4$, $Ti(OC_4H_9)_4$, $Ti(2-ethylhexoxy)_4$, $ZrCl_4$, $Zr(OC_2H_5)$ $_4$, $Zr(OC_3H_7)_4$, $ZR(O—i—C_3H_7)_4$, $Zr(OC_4H_9)_4$, $Zr(2$-ethylhexoxy$)_4$ and $ZrOCl_2$.

Further hydrolyzable compounds which can be employed for preparation of the systems according to the invention are, for example, boron trihalides and boric acid ester, such as, for example, $BCl_3$, $B(OCH_3)_3$ and $B(OC_2H_5)_3$, tin tetrahalides and tin tetraalkoxides, such as, for example, $SnCl_4$ and $Sn(OCH_3)_4$, and vanadyl compounds, such as, for example, $VOCl_3$ and $VO(OCH_3)_3$.

By the use according to the invention of hydroxyzable compounds other than silicon compounds, it is possible to integrate heteroatoms into the inorganic network and thus to adapt the properties of the systems according to the invention to the requirements of the particular case of use, for example in respect of cathode-ray opacity, thermal expansion and the like.

One or more components of the self-curing systems according to the invention furthermore can contain monomers which can undergo thermal and/or radiation-induced copolymerization. Spiro-orthoesters, spiro-orthocarbonates, bicyclic spiro-orthoesters, mono- or oligoepoxides, epoxysilanes or vinyl ethers are particularly preferred.

It is furthermore possible to add monomers which can undergo self-curing copolymerization to one or more components of the systems according to the invention.

The silanes of the general formulae I and Ia are processed either by themselves or together with other hydrolytically condensable and, if appropriate, polymerizable components by hydrolytic condensation to give the self-curing systems according to the invention, final curing of which is then carried out by polymerization of the polymerizable groups, this polymerization proceeding via a linkage of the C=C double bonds of the radical B in the case of silanes of the general formulae I and Ia and by a ring opening of the 1,4,6-trioxaspiro-[4.4]-nonane groups in the case of the spiro-silanes of the general formula III.

The silanes of the general formulae I, Ia, II (which can also contain polymerizable groups, such as, for example, C=C or epoxide groups), III and, for example, the titanium, zirconium and aluminum compounds of the general formulae IV and V contain hydrolyzable groups X or $R^0$, for example alkoxy groups, through which an inorganic network is built up during hydrolytic condensation, while the C=C double bonds contained in the radical B and the spiro groups contained in the radical Y form an organic network during the polymerization. The inorganic network can additionally be modified by addition of further hydrolytically condensable compounds and the organic network can be additionally modified by addition of further copolymerizable compounds. The cured systems according to the invention thus form an inorganic-organic matrix, into which further components, such as, for example, fillers or pigments, can be incorporated if required.

For building up the inorganic network or for preparation of the self-curing systems according to the invention, the silanes of the general formula I and/or Ia, if appropriate with addition of the silanes of the formula II and/or III and other cocondensable components, and if appropriate in the presence of a catalyst and/or a solvent, are hydrolyzed and polycondensed by the action of water or moisture. This polycondensation is preferably carried out by the sol-gel process, such as is described, for example, in the Offenlegungsschriften DE 2758414, 2758415, 3011761, 3826715 and 3835968, and, with spiro compounds (silanes of the general formula III, copolymerizable spiro-orthoesters, spiro-orthocarbonates, bicyclic spiro-orthoesters, spiro-orthocarbonates, bicyclic spiro-orthoesters or methacryloyl spiro-orthoesters), is preferably carried out in a basic medium, and otherwise can also be carried out in an acid medium.

The self-curing systems according to the invention can be prepared in the manner customary in the field of poly (hetero)condensates. If practically exclusively silicon compounds are employed, the hydrolytic condensation can in most cases be carried out by a procedure in which the water required is added directly at room temperature or with gentle cooling (preferably with stirring and in the presence of a hydrolysis and condensation catalyst) to the silicon compounds to be hydrolyzed, which are present either as such or as a solution in a suitable solvent, and the resulting mixture is then stirred for some time (one to several hours).

If reactive compounds of Al, Ti or Zr, which can also be in complexed form, are present, stepwise addition of the water is as a rule advisable. The hydrolysis is as a rule carried out at temperatures of between $-20°$ and $130°$ C. preferably between $0°$ and $30°$ C. or the boiling point of any solvent employed, regardless of the reactivity of the compounds present. As already indicated, the best manner of the addition of water depends above all on the reactivity of the starting compounds employed. Thus, for example, the dissolved starting compounds can be slowly added dropwise to an excess of water, or water is added in one portion or in portions to the starting compounds, which are dissolved if appropriate. It may also be beneficial not to add the water as such but to introduce it into the reaction system with the aid of water-containing organic or inorganic systems. Introduction of the amount of water into the reaction mixture with the aid of adsorbents laden with moisture, for example molecular sieves, and of water-containing organic solvents, for example 80% strength ethanol, has proved to be particularly suitable in many cases. However, the water can also be added by a chemical reaction in which water is liberated during the course of the reaction. Examples of this are esterifications.

If a solvent is used, ketones, preferably lower dialkyl ketones, such as acetone or methyl isobutyl ketone, ethers, preferably lower dialkyl ethers, such as diethyl ether or dibutyl ether, tetrahydrofuran, amides, esters, in particular ethyl acetate, dimethylformamide, amines, in particular triethylamine, and mixtures thereof are suitable, in addition to the lower aliphatic alcohols (for example ethanol or i-propanol).

If spiro-silanes of the general formula III are employed for preparation of the self-curing systems according to the invention, the hydrolysis is preferably carried out in a medium which is basic with respect to these silanes. This is generated either by a basic solvent, such as, for example, triethylamine, or by addition of basic hydrolysis and condensation catalysts, such as, for example, $NH_3$, NaOH, KOH, methylimidazone and the like.

The starting compounds to not necessarily all have to be present at the start of the hydrolysis (polycondensation), but in certain cases it may even prove to be advantageous if only a portion of these compounds is first brought into contact with water and the remainder of the compounds is added later.

In order to avoid precipitates as far ass possible during the hydrolysis and polycondensation when hydrolyzable compounds other than silicon compounds are used, the water can be added in several stages, for example in three stages. In this case, in the first stage, for example, one tenth to one twentieth of the amount of water required for the hydrolysis can be added. After brief stirring, one fifth to one tenth of the amount of water required can be added and, after further brief stirring, the remainder can finally be added.

The condensation time depends on the particular starting components and the proportions thereof, any catalyst used, the reaction temperature and the like. In general, the polycondensation is carried out under normal pressure, but it can also be carried out under increased or under reduced pressure.

The polycondensate thus obtained is stable to storage and, after addition of starter or activator systems, can be employed either as such or after partial or virtually complete removal of the solvent used or of the solvent formed during the reaction as a self-curing system or as a component in self-curing systems. In some cases, it may prove to be advantageous for the excess water and the solvent formed and any solvent additionally added in the product obtained after the polycondensation to be replaced by another solvent in order to stabilize the polycondensate. For this purpose, the reaction mixture can be concentrated, for example in vacuo at slightly elevated temperature (up to no m ore than 80° C.), to the extent that it can still be taken up in another solvent without problems.

To build up the organic network or to cure the systems according to the invention, the polycondensate according to the invention is polymerized, after addition of starter and/or activator systems and if appropriate after addition of other copolymerizable compounds and of fillers and other additives, it also being possible for thermal and/or radiation-induced curing additionally to be carried out, as well as self-curing, if corresponding monomers are added.

The final curing of the systems according to the invention is carried out, in the case of one-component systems, either by addition of a starter/activator system immediately before curing or by immediate addition of a starter to a system which already contains an activator or by immediate addition of an activator to a system containing a starter. In the case of multi-component systems, the final curing is carried out by mixing the individual components which contain starter or activator systems. In the course of free radical polymerization, the C=C double bonds of the silanes according to the formula I and/or Ia are thereby linked, and if silanes of the general formula III are present, the rings of the spiro groups are opened in the course of cationic polymerization.

Starter/activator systems which can be employed for the self-curing are both customary for such systems, such as, for example, aromatic amines (for example N,N-bis-(2-Hydroxy-ethyl)p-toluidine) as activators or as starters, for example, dibenzoyl peroxide, it being possible for the curing time of the systems according to the invention to be adjusted according to the requirements of the particular case of use via the concentration of the starter/activator systems and via the concentration ratio thereof.

The provision of those self-curing systems which can be cured the toxicologically acceptable activators is achieved by the combination of the systems according to the invention with silane-bonded tertiary amines of the general formula IX or X.

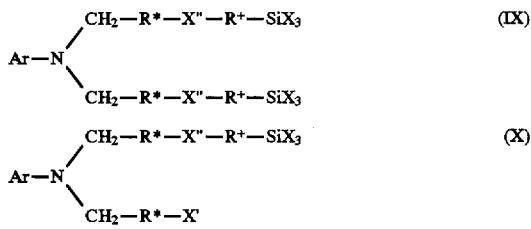

The radicals have the following meaning:
Ar=aryl, preferably phenyl, naphthyl or biphenyl,
R*=alkylene having 1 to 10, preferably 1 to 4 C atoms,
R+=alkylene having 0 to 10, preferably 0 to 4, C atoms,
X=as defined in the case of formulae I and Ia,
X'=—OH, —NH$_2$, —SH, —CH=CH$_2$, —C(O)—O—C(O)—R$^-$, —CH—CH$_2$—R$^-$, —NCO,
R$^-$=alkyl with 1 to 10, preferably 1 to 4, C atoms,
X"=—O—C(O)—NH—, —NH—C—(O)—NH—, —S—C(O)—NH—, —O—CH$_2$—CHOH—, —NH—CH$_2$—CHOH—, —S—CH$_2$—CHOH—, —O—C(O)—, —NH—C(O)—, —S—C(O)—, —C$_2$H$_4$—, —C$_2$H$_4$—S—, C$_2$H$_4$—NH—, —NH—C(O)—O—, —NH—C(O)—S—, —CHOH—CH$_2$—O—, —CHOH—CH$_2$—NH—, —CHOH—CH$_2$—S—, —C(O)—O—, —C(O)—NH—, —C(O)—S—, it also being possible for the radicals Ar, R*, R$^-$ or R+ to carry substituents.

Preferred embodiments of the activators according to the invention are

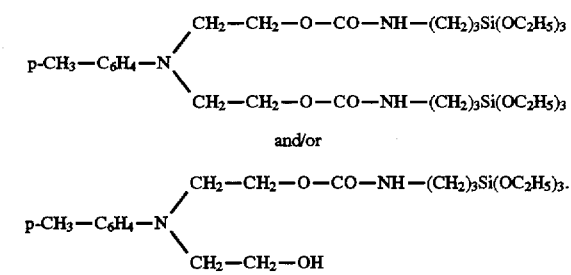

Surprisingly, it has been found that amines of the general formula IX or X can likewise be employed as activators and lead to self-curing of the systems according to the invention. This is all the more surprising since, for example, the silane-bonded amine of the formula (C$_2$H$_5$)$_2$N(CH$_2$)$_3$Si(OC$_2$H$_5$)$_3$ does not lead to self-curing.

The use of amines of the formula IX or X offers the great advantage that the amine component is incorporated into the inorganic network, and firmly anchored there, via the silane content during the hydrolysis and the condensation. After curing, not free amines are thus present, and not toxicological problems occur in this respect. The systems according to the invention using amines of the formula IX are therefore suitable as activators in particular for use in the medical sector.

If activators of the formula IX or X are used, there is the great advantage of the systems according to the invention that both the activator silanes according to the invention and the reactive monomers of the formula I and/or Ia are firmly anchored, i.e. chemically bonded, that is to say are not longer present in the free state, in the inorganic-organic network after curing and are thus toxicologically acceptable. The combination of reactive monomers of the formula I and/or Ia with the activator silanes of the formula IX or X according to the invention thus offers quite considerable toxicological advantages over the prior art.

The amines of the formula IX or X according to the invention are prepared, for example, via addition reactions, amines of the formula IX or X or mixtures thereof being formed, depending on the amount of silane added (1 to 2 equivalents). Various types of addition reactions which lead to the activator silanes according to the invention are shown by equation using the example of the reaction of one equivalent of amine with two equivalents of silane.

Type 1:
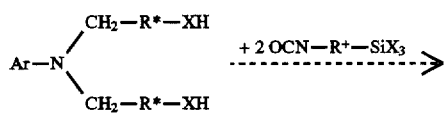 + 2 OCN—R⁺—SiX₃ ⇢
mit X = O, NH, NR oder S.
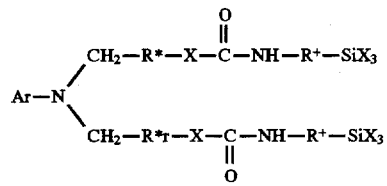
where X = O, NH NR or S.
Type 2:
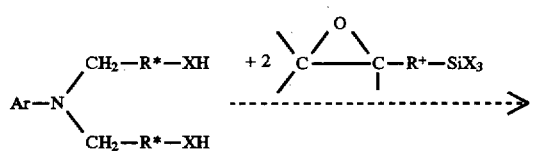 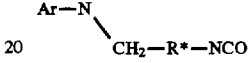 ⇢
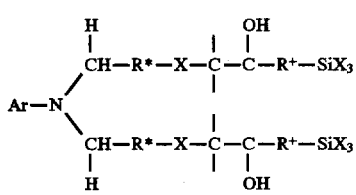
where X = O, NH, NR or S.
Type 3:
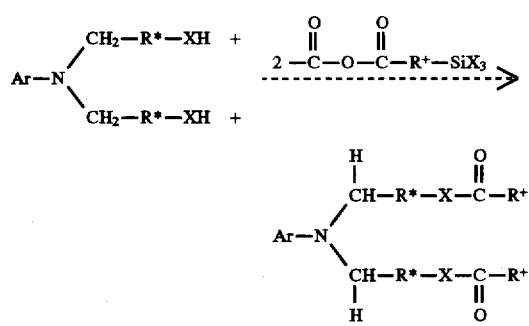
where X = O, NH, NR or S.
Type 4:
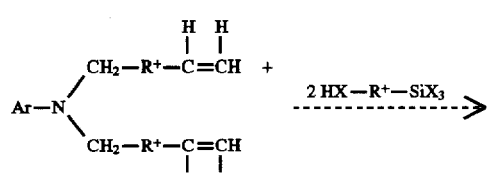 ⇢
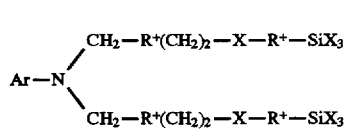
where X = S, NR or NH.
Type 5:
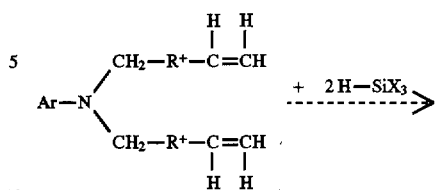 + 2 H—SiX₃ ⇢
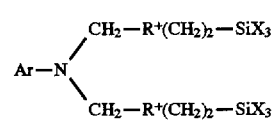
Type 6:
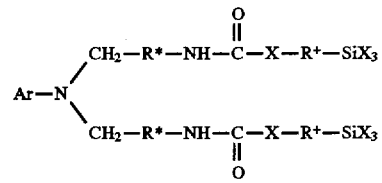 + 2 HX—R⁺—SiX₃ ⇢
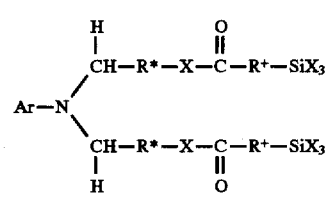
where X = O, NH, NR or S.
Type 7:
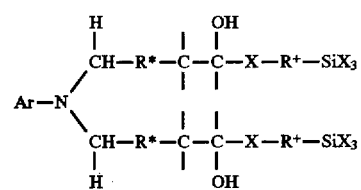
where X = O, NH, NR or S.
Type 8:
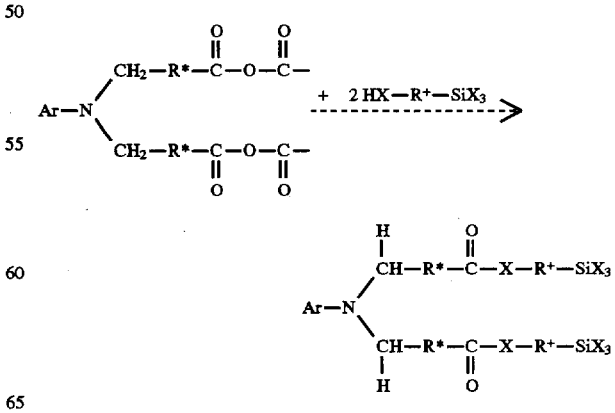
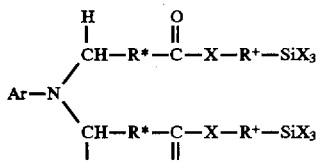
where X = O, NH, NR or S.

Type 9:

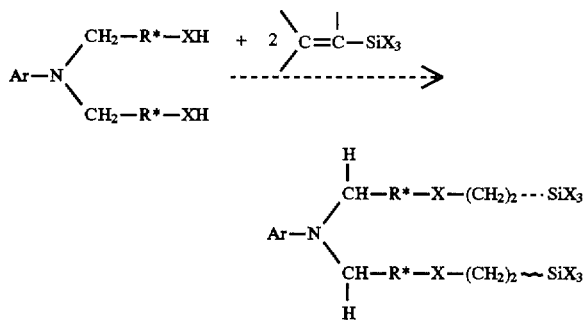

where X = NH, NR or S.

It is also possible to add further compounds which can be polymerized ionically and/or by free radicals to the systems according to the invention before the final curing, that is to say before the polymerization. Monomers which can be polymerized by free radicals and which can be added are, for example, those having C=C double bonds, such as, for example, acrylates or methacrylates, polymerization taking place via the C=C double bonds. Compounds which can be polymerized ionically and which can be added contain, for example, ring systems which can be polymerized cationically and by ring opening, such as, for example, spiro-orthoesters, spiro-orthocarbonates, bicyclic spiro-orthoesters and mono- or oligoepoxides. However, it is also possible to add compounds which can be polymerized both cationically and by free radicals, such as, for example, methacryloyl spiro-orthoesters. These can be polymerized by free radicals via the C=C double bond and cationically by ring opening. These systems are described, for example, in Journal f. prakt. Chemie, Volume 330, Issue 2, 1988, pages 316–318, or in Journal of Polymer Science: Part C: Polymer Letters, Vol. 26, pages 517–520 (1933).

If photochemical curing also takes place, in addition to the self-curing of the systems according to the invention, customary cationic photoinitiators are added to at least one component of the system according to the invention. Suitable photoinitiators according to the prior art are, for example, compounds which liberate acids on irradiation, such as, for example, $C_6H_5$—$N_2BF_4$, o—$NO_2$—$C_6H_4$—$CH_2$—O—$SO_2CF_3$, or triarylsulfonium salts of the general formulae VI, VII and VIII, in which the radicals Ar can be identical or different and denote aryl or arylene, for example phenyl and phenylene, where X—=$BF_4$—, $AsF_6$—, $PF_6$— or $SbF_6$—.

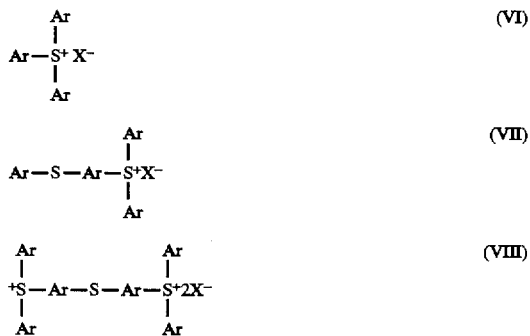

These photoinitiators are commercially obtainable, for example triphenylsulfonium hexafluorophosphate as a 50% strength solution in propylene carbonate under the commercial name UVI-6990 from Union Carbide, or KI-85 (initiator according to formula VIII where Ar=phenyl or phenylene and X—=$PF_6$— as a 50% strength solution in propylene carbonate) from Degussa. In principle, all photoinitiators which are employed for polymerization of oxirane-containing molecules such as, for example, cycloaliphatic epoxides, are suitable.

Under the influence of the irradiation, the triarylsulfonium salt is subjected to photolysis, and a Broensted acid which catalyzes ring opening of the spiro groups is formed, the composition polymerizing.

If thermal curing of the systems according to the invention also takes place in addition to self-curing, thermal initiators are added to at least one component of the system according to the invention. Suitable thermal initiators are, for example, $BF_3$ as $BF_3H_2NC_2H_5$, $ZnCl_2$, $TiCl_4$ or $SnCl_2$. Here also, all the thermal initiators which are suitable for polymerization of epoxide groups can be employed.

The initiators are added in customary amounts.

Photoinitiators which can be employed are, for example, those which are commercially obtainable. Examples of these are Iracure 184 (1-hydroxycyclohexyl phenyl ketone), Iracure 500 (1-hydroxycyclohexyl phenyl ketone/benzophenone) and other photoinitators of the Iracure type obtainable from Ciba-Geigy; Darocure 1173, 1116, 1398, 1174 and 1020 (obtainable from Merck), benzophenone,2-chlorothioxanthone, 2-methylthioxanthone, 2-isopropylthioxanthone, benzoin, 4,4'-dimethoxybenzoin, camphorquinone and others.

Possible thermal initiators are, in particular, organic peroxides in the form of diacyl peroxides, peroxydicarbonates, alkyl peresters, dialkyl peroxides, perketals, ketone peroxides and alkyl hydroperoxides. Concrete and preferred examples of thermoinitiators are dibenzoyl peroxide, t-butyl perbenzoate and azobisisobutyronitrile.

The inorganic network is responsible for the cured systems according to the invention already having an outstanding abrasion resistance and dimensional stability entirely without addition of fillers, and the formation of the organic network has the effect of a low or even negative volume shrinkage. If silanes of the general formula III are added, the change in volume during curing can be adapted to the requirements of the particular case of use by the number of spiro groups in the systems according to the invention, i.e. by the nature and/or by the amount of spiro-silanes of the general formula III employed. The higher the number of spiro groups, the lower the volume shrinkage. It is indeed even possible to influence the change in volume during curing such that an increase in volume results.

The self-curing systems according to the invention can be processed either as such or together with customary additives, such as, for example, fillers, adhesion promoters or pigments. The advantageous properties of the cured systems according to the invention are thereby improved still further by addition of fillers, so that material sin which the properties profile is improved quite considerably compared with prior art and which can meet all the requirements imposed on such materials result from them.

Fillers which can be employed are, for example, macrofillers (of glass, ceramic or quartz, particle sizes of between 2 and 50 µm), homogeneous microfillers (for example of pyrogenic silicic acid, particle sizes about 0.04 µm), non-homogeneous microfillers (some of the pyrogenic silicic acid is present as polymer chips), hybrid fillers (mixture of macro- and microfillers) or extra-fine hybrid fillers (for example mixture of Aerosil and Ba glass or Sr glass with particle sizes of 2 µm). The mechanical properties of the resulting cured systems are influenced at the same time by the particle size and the amount of fillers. The addition of fillers also positively influences shrinkage (the higher the filler content in the same matrix, the lower the shrinkage), the X-ray opacity (by addition of, for example, Ba components, Sr components, Ti components or Zr components in the filler) and the coefficient of thermal expansion (dependent on the filler content; fillers usually have a lower coefficient of expansion than the organic matrix).

It is furthermore possible to add cured systems according to the invention in finely divided form as a filler to non-cured systems according to the invention. For this, the systems according to the invention are polymerized for example in the form of an emulsion, precipitation, solution or suspension polymerization. The polymer is dried, finely ground if appropriate, and admixed to the systems according to the invention.

Systems according to the invention are illustrated in more detail with the aid of the following examples.

EXAMPLE 1

Reaction Equation

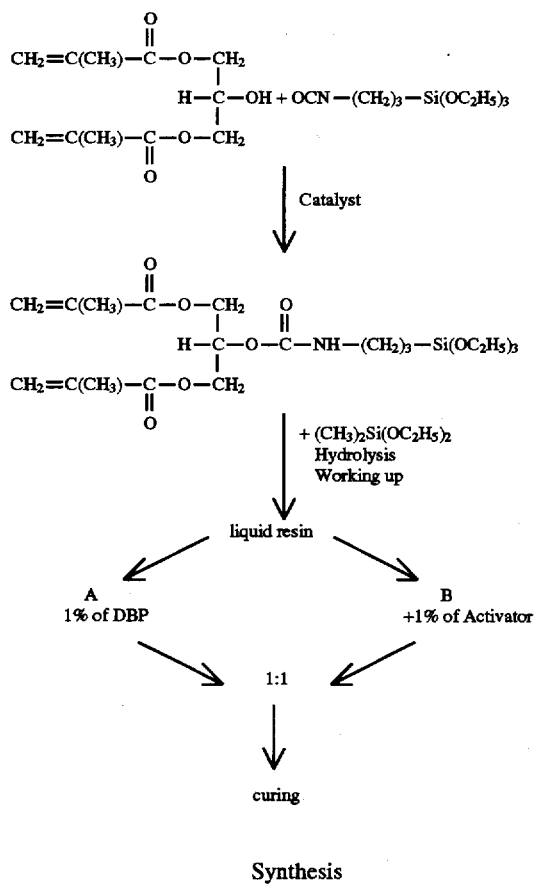

Synthesis 12.4 g (0.05 mol) of 3-isocyanatopropyltriethoxy-silane are added dropwise to an initial mixture of 11.4 g (0.05 mol) of glycerol 1,3-dimethacrylate and dibutyltin dilaurate (as an addition catalyst) at room temperature under dry air. After stirring for about 2 hours, the addition is complete (IR control), and 7.4 g (0.05 mol) of dimethyldiethoxysilane are added. About 100 ml of ethyl acetate and 3.6 g of water (including catalysts) are added for hydrolysis and condensation. After stirring at room temperature for about 1 day, the moisture is extracted by shaking with water and filtered, the filtrate is evaporated on a rotary evaporator and the residue is freed completely from volatile constituents using an oil pump. The clear, virtually colorless resin is obtained in a yield of about 95% and can be employed in this state for subsequent curing.

Preparation of the Curing Agent Components

1% of dibenzoyl peroxide (starter) is dissolved in 5 g of the above resin. This gives component A. 1% of N,N-bis-(2-hydroxyethyl)-p-toluidine (activator) is dissolved in a further 5 g of the above resin. This gives component B.

Curing

1st Example: Components A and B are dissolved in one another and introduced into a curing mold (Ø=2 cm; d=2 mm). After about 1–2 minutes, the sample becomes hard, and curing has taken place after about 5 minutes.

2nd Example: An adhesive bond is produced as follows. The two surfaces for gluing are brushed with component A or B respectively or a mixture of both and pressed together. After about 5 minutes, a stable adhesive bond exists.

The curing time and therefore the processing time can be varied and controlled by the particular amount of starter and activator and by the ratio thereof.

EXAMPLE 2

Reaction Equation

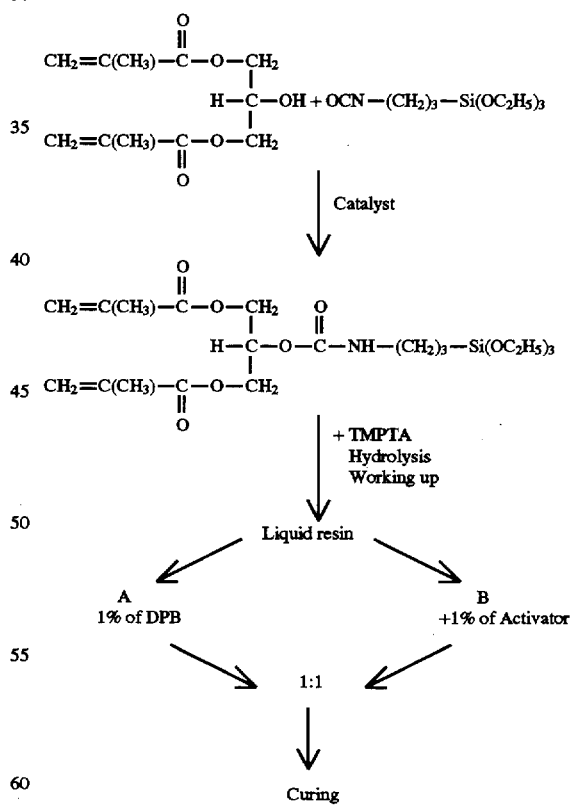

Synthesis 123.7 g (0.5 mol) of 3-isocyanatopropyltriethoxy-silane are added dropwise to an initial mixture of 114.1 g (0.5 mol) of glycerol 1,3-dimethacrylate and dibutyltin dilaurate (as an addition catalyst) at room temperature under dry air. After stirring for about 2 hours, the addition is complete (IR control). About 1000 ml of ethyl acetate and 21.6 g of water (including catalysts) are added for the hydrolysis and condensation. 29.6 g (0.2 mol) of trimethylolpropyl triacrylate (TMPTA) are added as a reactive solvent. After stirring at room temperature for about 1 hour, the mixture is extracted by shaking with water and filtered, the filtrate is evaporated on a rotary evaporator and the residue is freed completely from volatile constituents using an oil pump. The clear, virtually colorless resin is obtained in a yield of about 94% and can be employed in this state for subsequent curing.

Preparation of the Curing Agent Components

1% of dibenzoyl peroxide (starter) is dissolved in 5 g of the above resin. This gives component A. 1% of N,N-bis-(2-hydroxyethyl)-p-toluidine (activator) is dissolved in a further 5 g of the above resin. This gives component B.

Curing

1st Example: Components A and B are dissolved in one another and introduced into a curing mold (∅=2 cm; d=2 mm). After about 1–2 minutes, the sample becomes hard, and curing has taken place after about 4 minutes.

2nd Example: An adhesive bond is produced as follows. The two surfaces for gluing are brushed with component A or B respectively or a mixture of both and pressed together. After about 4 minutes, a stable adhesive bond exists.

The curing time and therefore the processing time can be varied and controlled by the particular amount of starter and activator and by the ratio thereof.

EXAMPLE 3

Preparation of the Activator Silane

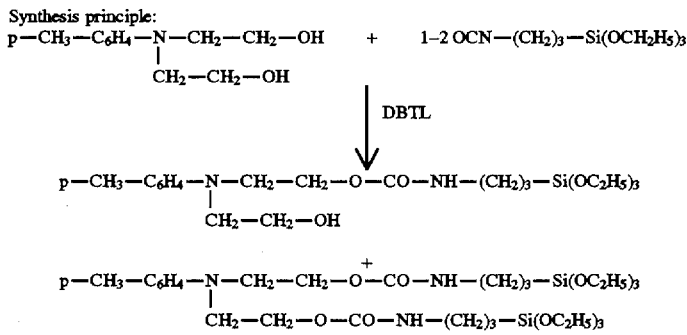

Synthesis Instruction 7.4 g (0.03 mol) of 3-isocyanatopropyltriethoxy-silane are added dropwise to an initial mixture of 3.9 g (0.02 mol) of N,N-bis-(2-hydroxyethyl)-p-toluidine (activator form example 2) and DBTL (dibutyltinlaurate) as the catalyst dissolved in ethyl acetate, at room temperature. After stirring for 2 hours, the addition is complete (IR control). For characterization, the solvent is stripped off.

IR data:
ν(NH, urethane)=3380 cm$^{-1}$
ν(CH, aliphatic)=2980–2880 cm$^{-1}$
ν(CH, aromatic)>3000 cm$^{-1}$
ν(C=O, urethane)=1703 cm$^{-1}$ The activator silane can be employed in the pure form or else directly in the form of the synthesis solution.

EXAMPLE 4

Curing by Means of Activator Silane Without Prior Hydrolysis

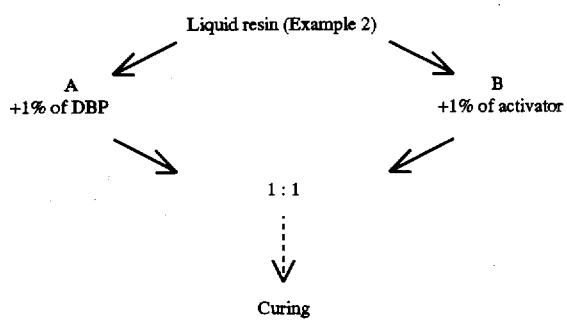

Preparation of the Curing Agent Components

1% of dibenzoyl peroxide is dissolved in 2 g of the above resin (see Example 2) ≙ component A). The activator silane (1%) is likewise dissolved in 2 g of the resin (≙component B).

Curing

Components A and B are dissolved in one another and introduced into a curing mold (∅=2 cm, d=2 mm). The sample becomes hard after about 10 minutes.

EXAMPLE 5

Inorganically Co-condensed Activator Silane

Reaction equation:

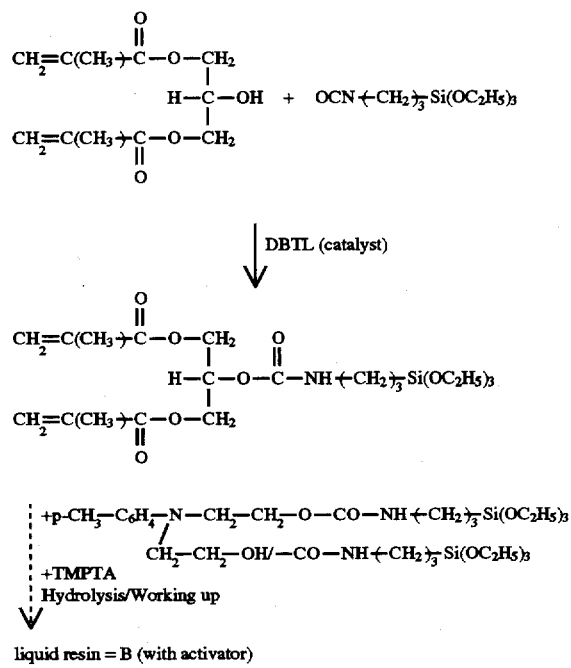

liquid resin = B (with activator)

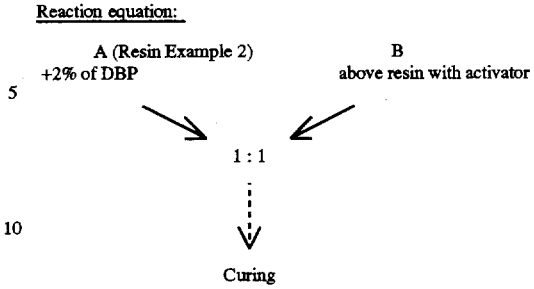

Synthesis 49.5 g (0.2 mol) of 3-isocyanatopropyltriethoxy-silanes are added dropwise to an initial mixture of 45.6 g (0.2 mol) of glycerol 1,3-dimethyl acrylate [sic] and dibutyltin dilaurate (as the addition catalyst) at room temperature under dry air. After stirring for about 2 hours, the addition is complete (IR control) and about 200 ml of ethyl acetate, 11.9 g (0.04 mol) of TMPTA and 1.7 g (0.003 mol) of activator silane (according to Example 3) are added. About 8.8 g of water (including catalyst) are added for the hydrolysis and condensation. After stirring at room temperature for about 1 day, the mixture is extracted by shaking with water and filtered, the filtrate is evaporated on a rotary evaporator and the residue is freed completely from volatile constituents using an oil pump. The clear, virtually colorless resin is obtained in a yield of about 95% and can be employed in this state for subsequent curing.

The addition of isocyanate onto the methacrylate and the amine can also be carried out in one batch mixture.

Preparation of the Curing Agent Components

2% of dibenzoyl peroxide are dissolved in 6 g of the resin from Example 2 (≙component A). 6 g of the above resin with the activator silane form component B. The dibenzoyl peroxide can also function as component A directly, i.e. without addition of resin.

Curing

Components A and B are dissolved in one another and introduced into a curing mold (∅=2 cm, d=2 mm). After about 3–4 minutes, the sample becomes hard. The curing time and therefore the processing time can be varied by the particular amount of starter and activator and the ratio thereof.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 4310733.8, for which benefit under 35 USC §119 is claimed, also is expressly incorporated herein in its entirety.

What is claimed is:

1. A self-curing system based on polymerizable and hydrolytically condensable or hydrolytically condensed silicon compounds, wherein said system required no thermal or radiation-induced photoinitiators for polymerization, comprising:

A. an aromatic amine activator; and
B. at least one silicon compound of the formula I or Ia, $$\{X_a R_b Si[R'(A)_c]_{(4-a-b)}\}_x B \quad (I)$$

$$\{X_a R_b Si[(R'A)_c]_{(4-a-b)}\}_x B \quad (Ia)$$

or a hydrolytically precondensed form of said silicon compound,
wherein the radicals and integers are identical or different and have the following meaning:
A=O, S, PR", POR", NHC(O)O or NHC(O)NR",
B=a straight-chain or branched organic radical which is derived from a compound B', said compound B' comprising at least 5 to 50 carbon atoms, and having at least two C=C double bonds, except when c=1 and A=NHC(O)O or NHC(O)NR" in which case compound B' comprises at least one double bond,
R=alkyl, alkenyl, aryl, alkylaryl or arylalkyl,
R'=alkylene, arylene or alkylenearylene,
R"=hydrogen, alkyl or aryl,
X=hydrogen, halogen, hydroxyl, alkoxy, acyloxy, alkylcarbonyl, alkoxycarbonyl or NR"$_2$,
a=1, 2 or 3,
b=0, 1 or 2,
c=0 or 1,
x=an integer, the maximum value of which corresponds to the number of double bonds in the compound B' minus 1, or equals the number of double bonds in the compound B', if c=1 and A represents NHC(O)O or NHC(O)NR";
wherein said alkyl and alkenyl radicals are substituted or unsubstituted straight-chain, branched or cyclic radicals having from 1 to 20 carbon atoms, aryl is substituted or unsubstituted phenyl, naphthyl or biphenyl, and said alkoxy, acyloxy, alkylcarbonyl, alkoxycarbonyl, alkylaryl, arylalkyl, arylene, alkylene and alkylenearyl radicals are derived form the alkyl and aryl radicals defined above.

2. A self-curing system according to claim 1, wherein,
X=(C$_1$–C$_4$)-alkoxy or halogen;
R=(C$_1$–C$_4$)-alkyl;
R'=(C$_1$–C$_4$)-alkylene;
A=O, S or NHC(O)O;
a=1, 2 or 3;
c=0 or 1;
4–a–b=0 where c=0; or
4–a–b=1 where c=1.

3. A self-curing system according to claim 1, wherein $\{X_a R_b Si[(R'A)_c]_{(4-a-b)}\}$ is selected from the group consisting of triethoxysilyl, methyldiethoxysilyl, methyldichlorosilyl, 3-methyldimethoxysilyl-propylthio, 3-triethoxysilyl-propylthio, ethoxydimethylsilylmethylthio, methyldiethoxysilyl-methylthio and 3-triethoxysilylpropylurethane.

4. A self-curing system according to claim 1, wherein B is derived from a substituted or unsubstituted compound B' having at least two groups which are acrylate, methacrylate or a combination thereof, and wherein B is selected from the group consisting of acrylic acid esters of trimethylolpropane, pentaerythritol, dipentaerythritol, C$_2$–C$_4$ alkanediols, polyethylene glycols, polypropylene glycols, and bisphenol A which may be substituted or unsubstituted.

5. A self-curing system according to claim 1, further comprising at least one compound of the general formula (II), or a hydrolytically precondensed form thereof, $$R_x(R^2Z)_y SiX_{4-(x+y)} \quad (II)$$

wherein the radicals and indices are identical or different and have the following meaning:
R=alkyl, alkenyl, aryl, alkylaryl or arylalkyl,
R$^2$=alkylene or alkenylene, wherein one or more of the carbon atoms of the alkylene or alkenylene may be interrupted by oxygen atoms, sulfur atoms or —NH— groups,
R"=hydrogen, alkyl or aryl,
X=hydrogen, halogen, hydroxyl, alkoxy, acyloxy, alkylcarbonyl, alkoxycarbonyl or NR"$_2$,
Z=halogen or an optionally substituted amino, amide, aldehyde, alkylcarbonyl, carboxyl, mercapto, cyano, alkoxy, alkoxycarbonyl, sulfonic acid, phosphoric acid, acryloxy, methacryloxy, epoxy or vinyl group,
x=0, 1, 2 or 3,
y=0, 1, 2 or 3, where x+y=1, 2 or 3.

6. A self-curing system according to claim 1, further comprising at least one compound of the general formula III, or a precondensed form thereof, $$Y_n SiX_m R_{4-(n+m)} \quad (III)$$

in which the radicals and integers are identical or different and have the following meaning:
R=alkyl, alkenyl, aryl, alkylaryl or arylalkyl,
X=hydrogen, halogen, hydroxyl, alkoxy, acyloxy, alkylcarbonyl, alkoxycarbonyl or NR"$_2$,
R"=hydrogen, alkyl or aryl,
Y=a substituent which contains a substituted or unsubstituted 1,4,6-trioxaspiro-[4,4]nonane radical,
n=1, 2 or 3,
m=1, 2 or 3, where n+m≦4.

7. A self-curing system according to claim 1, further comprising at least one aluminum, titanium or zirconium compound, or a precondensed form thereof, of the general formula IV or V, $$(IV) Alr°_3 MX_k R_1 \quad (V)$$

in which the radicals and integers are identical or different and have the following meaning:
M=titanium or zirconium
R°=halogen, hydroxyl, alkoxy or acyloxy,
k=1, 2, 3 or 4,
l=0, 1, 2 or 3, and
X and R are as previously defined in claim 1.

8. A self-curing system according to claim 1, further comprising a copolymerization component selected from the group consisting of monomers, oligomers, polymers, and mixtures thereof, which component can undergo thermal copolymerization, radiation-induced copolymerization, or both.

9. A self-curing system according to claim 8, wherein said copolymerization component is selected from the group consisting of spiro-orthoesters, spiro-orthocarbonates, bicyclic spiro-orthoesters, mono- or oligoepoxides, epoxysilanes and vinyl ethers.

10. A self-curing system according to claim 1, wherein the composition comprises a self-curing component selected from the group consisting of monomers, oligomers, polymers, and mixtures thereof, which are self-curing.

11. A self curing system according to claim 1, wherein said activator comprises at least one silane selected from group consisting of silanes of general formula IX and silane of the general formula X,

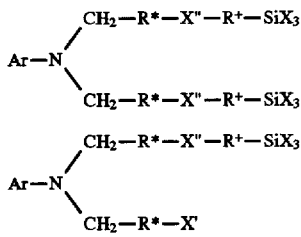

in which the radicals have the following meaning:
Ar=aryl;
R*=alkylene having 1 to 10 C atoms,
R+=alkylene having 0 to 10 atoms,
X=as defined in claim 1,
X'=—OH, —NH₂, —SH, —CH=CH₂, —C(O)—O—C(O) R,

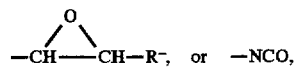

R⁻=alkyl with 1 to 10 C atoms,
X"=—O—C(O)—NH—, —NH—C(O)—NH—, —S—C(O)—NH—, —O—CH₂—CHOH—, —NH—CH₂—CHOH—, —S—CH₂—CHOH—, —O—C(O)—, —NH—C(O)—, —S—C(O)—, —C₂H₄—, —C₂H₄—S—, —C₂H₄—NH—, —NH—C(O)—O—, —NH—C(O)—S—, —CHOH—CH₂—O—, —CHOH—CH₂—NH—, —CHOH—CH₂—S—, —C(O)—O—, —C(O)—NH—, or —C(O)—S—,
wherein one or more of Ar, R*, R⁻ and R+ may be substituted.

12. A self-curing system according to claim 11, comprising at least one compound selected from the group consisting of:

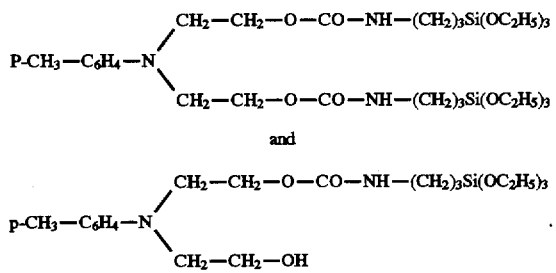

13. A method using a self-curing system according to claim 1, wherein said method comprises the step of applying said composition in a process selected from the group consisting of casting, gluing, sealing coating, shaping, producing fillers, molding, bonding, and producing fibers or films.

14. Silanes of the general formula IX or X,

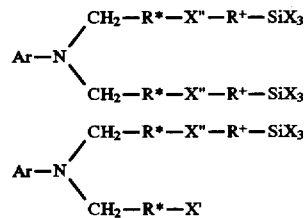

in which the radicals have the following meaning:
Ar=aryl;
R*=alkylene having 1 to 10 C atoms,
R+=alkylene having 0 to 10 C atoms,
X=hydrogen, halogen, hydroxyl, alkoxy, acyloxy, alkylcarbonyl, alkoxycarbonyl or NR"₂,
X'=—OH, —NH₂, —SH, —CH=CH₂, —C(O)—O—C(O) —R⁻,

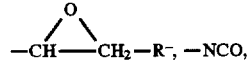

R⁻=alkyl with 1 to 10 C atoms,
X"=—O—C(O)—NH—, —NH—C(O)—NH—, —S—C(O)—NH—, —O—CH₂—CHOH—, —NH—CH₂—CHOH—, —S—CH₂—CHOH—, —O—C(O)—, —NH—C(O)—, —S—C(O)—, —C₂H₄—, —C₂H₄—S—, —C₂H₄—NH—, —NH—C(O)—O—, —NH—C(O)—S—, —CHOH—CH₂—O—, —CHOH—CH₂—NH—, —CHOH—CH₂—S—, —C(O)—O—, —C(O)—NH—, or —C(O)—S—,
wherein one or more of Ar, R*, R⁻ or R+ may be substituted.

15. A silane according to claim 14, wherein
Ar=phenyl, naphthyl or biphenyl,
R*=alkylene having 1 to 4 C atoms,
R+=alkylene having 0 to 4 C atoms, and
R⁻=alkyl having 1 to 4 C atoms.

16. A method of making a self-curing system comprising combining (i) an activator, and (ii) a precondensed form of at least one silicon compound of the formula I or Ia,

in which the radicals and integers are identical or different and have the following meaning:
A=O, S, PR", POR", NHC(O)O or NHC(O)NR",
B=a straight-chain or branched organic radical which is derived from a compound B', said compound B' comprising at least 5 to 50 carbon atoms, and having at least two C=C double bonds, except when c=1 and A=NHC(O)O or NHC(O)NR" in which case compound B' comprises at least one double bond,
R=alkyl, alkenyl, aryl, alkylaryl or arylalkyl,
R'=alkylene, arylene or alkylenearylene,
R"=hydrogen, alkyl or aryl,
X=hydrogen, halogen, hydroxyl, alkoxy, acyloxy, alkylcarbonyl, alkoxycarbonyl or NR"₂,
a=1, 2 or 3,
b=0, 1 or 2,
c=0 or 1,
x=an integer, the maximum value of which corresponds to the number of double bonds in the compound B' minus 1, or equals the number of double bonds in the compound B', if c=1 and A represents NHC(O)O or NHC(O)NR";
wherein the above alkyl and alkenyl radicals are optionally substituted straight-chain, branched or cyclic radicals having from 1 to 20 carbon atoms, aryl represents optionally substituted phenyl, naphthyl or biphenyl, and the above alkoxy, acyloxy, alkylcarbonyl, alkoxycarbonyl, alkylaryl, arylalkyl, arylene, alkylene and alkylenearyl radicals are derived from the alkyl and aryl radicals defined above.

17. A method of making a self-curing system, comprising the step of combining a silane aromatic amino activator of general formula IX or X as defined in claim 11 with a polymerizable reactive monomer of general formula I, Ia, II, or III as defined in any one of claim 1, 5 or 6.

18. A self-curing system according to claim 1, further comprising both a starter and an activator.

19. A method of final curing of a one component self-curing system comprising the alternate steps of (i) adding a starter or activator system immediately before the curing step; (ii) immediately adding a starter to a system that already contains an activator; or (iii) immediately adding an activator to a system already containing a starter, provided that said component is a hydrolytically precondensed form of at least one silicon compound of the formula I or Ia as defined in claim 1.

20. A method of final curing of a multicomponent self-curing polymer system according to claim 1 comprising the steps of:
  (A) producing a liquid resin by hydrolytically precondensing a cyano-substituted silane in the presence of an addition catalyst;
  (B) adding a starter to one portion of said liquid resin to produce a first reactant;
  (C) adding an activator to a second portion of said liquid resin to produce a second reactant; and,
  (D) mixing said first reactant with said second reactant.

* * * * *